(12) United States Patent
Chen et al.

US011487965B2

(10) Patent No.: US 11,487,965 B2
(45) Date of Patent: Nov. 1, 2022

(54) METHOD AND APPARATUS FOR COUNTING FOOT STEP BASED ON STRIDE FREQUENCY, AND DEVICE

(71) Applicant: HUAWEI TECHNOLOGIES CO., LTD., Guangdong (CN)

(72) Inventors: Yixin Chen, Shenzhen (CN); Chen Dong, Beijing (CN); Xiaohan Chen, Shenzhen (CN); Yu Wang, Beijing (CN); Fan Yang, Beijing (CN)

(73) Assignee: HUAWEI TECHNOLOGIES CO., LTD., Guangdong (CN)

( * ) Notice: Subject to any disclaimer, the term of this patent is extended or adjusted under 35 U.S.C. 154(b) by 345 days.

(21) Appl. No.: 16/640,829

(22) PCT Filed: Aug. 23, 2017

(86) PCT No.: PCT/CN2017/098591
§ 371 (c)(1),
(2) Date: Feb. 21, 2020

(87) PCT Pub. No.: WO2019/036927
PCT Pub. Date: Feb. 28, 2019

(65) Prior Publication Data
US 2021/0042121 A1   Feb. 11, 2021

(51) Int. Cl.
*G06K 9/62*       (2022.01)
*G01C 22/00*   (2006.01)
(Continued)

(52) U.S. Cl.
CPC .......... *G06K 9/6232* (2013.01); *A61B 5/1123* (2013.01); *G01C 22/006* (2013.01); *G06F 1/163* (2013.01)

(58) Field of Classification Search
CPC ... G06K 9/6232; A61B 5/1123; G01C 22/006
See application file for complete search history.

(56) References Cited

U.S. PATENT DOCUMENTS 6,145,389 A * 11/2000 Ebeling ................ G01C 22/006
                                                                  73/865.4
2006/0161079 A1    7/2006 Choi et al.
(Continued)

FOREIGN PATENT DOCUMENTS

CN    103175540 A      6/2013
CN    103792386 A  *  5/2014
(Continued)

OTHER PUBLICATIONS

Hao Lee,"Study of Activities Classify and Step Detection Base on the Three-Dimensional Acceleration Sensor",Tianjin University,dated Jun. 2011,total 49 pages.
(Continued)

*Primary Examiner* — John C Kuan
(74) *Attorney, Agent, or Firm* — WHDA, LLP

(57) ABSTRACT

A method includes: collecting an original signal in a specified time interval, and performing combined acceleration processing on the original signal to obtain a combined acceleration signal; performing state processing on the combined acceleration signal to obtain a motion time interval, and extracting a plurality of feature groups from the combined acceleration signal according to a preset motion rule; and performing screening on the plurality of feature groups to obtain a first feature group, extracting a median value from the first feature group, and obtaining a stride frequency in the specified time interval based on the median value and a collection frequency, and obtaining a quantity of steps through calculation based on the motion time interval and the stride frequency.

18 Claims, 16 Drawing Sheets

(51) Int. Cl.
  *A61B 5/11* (2006.01)
  *G06F 1/16* (2006.01)

(56) References Cited

U.S. PATENT DOCUMENTS

| | | |
|---|---|---|
| 2014/0032165 A1 | 1/2014 | Sarrafzadeh et al. |
| 2015/0185044 A1 | 7/2015 | Nie et al. |
| 2016/0209232 A1 | 7/2016 | Yang et al. |
| 2017/0188897 A1* | 7/2017 | Thein .................. G01P 15/00 |

FOREIGN PATENT DOCUMENTS

| | | |
|---|---|---|
| CN | 103983273 A | 8/2014 |
| CN | 104197952 A | 12/2014 |
| CN | 104406604 A | 3/2015 |
| CN | 103997572 B | 1/2016 |
| CN | 105496416 A | 4/2016 |
| CN | 103712632 B | 8/2016 |
| CN | 106289309 A | 1/2017 |
| CN | 106931990 A | 7/2017 |

OTHER PUBLICATIONS

Zhuang Wang, "A Human Activity Recognition Method for Wearable Device", dated Feb. 2017, Nanjing University of Posts and Telecommunications, total 68 pages.

Weidu Yang, "Research of Activity Recognition And State Monitoring Methods of The Human Based on Wearable Device", dated Feb. 2017, Harbin Institute of Technology, total 79 pages.

Office Action dated Aug. 19, 2020, issued in counterpart CN Application No. 201780082882.2, with English Translation. (18 pages).

Zhong S, Wang L, Bernardos A M, et al. "An accurate and adaptive pedometer integrated in mobile health application", [C]//Wireless Sensor Network, 2010. IET-WSN. IET International Conference on. IET, 2010: 78-83.

International Search Report dated May 18, 2018, issued in counterpart application No. PCT/CN2017/098591, with English Translation. (13 pages).

* cited by examiner

METHOD AND APPARATUS FOR COUNTING FOOT STEP BASED ON STRIDE FREQUENCY, AND DEVICE

CROSS-REFERENCE TO RELATED APPLICATIONS

This application is a national stage of International Application No.PCT/CN2017/098591, filed Aug. 23, 2017, which is hereby incorporated by reference in its entirety.

TECHNICAL FIELD

This application relates to the comminations field, and in particular, to a method and an apparatus for counting a foot step based on a stride frequency, and a device.

BACKGROUND

Under guidance of the national fitness program, running exercise is popular among people, and there is a huge market opportunity for wearable sports devices. A fitness record is a basic exercise and fitness function of the wearable sports device, and is mainly used to implement step counting, distance recording, exercise time recording, energy consumption calculation, and the like. Most users have a requirement for this function. The step counting is a most intuitive exercise indicator in the fitness record, so that the users can directly assess their respective exercise amounts. In addition, step counting is combined with a related social APP, and becomes an important part of exercise socialization.

Step counting is implemented when an existing wearable sports device is worn on the wrist and around the waist. For example, if a user wears the wearable sports device on the foot, step counting cannot be implemented. Therefore, an existing technical solution cannot implement foot step counting.

SUMMARY

A technical problem to be resolved in embodiments of this application is to provide a method for counting a foot step based on a stride frequency, to resolve a prior-art problem that foot step counting cannot be implemented According to a first aspect, a method for counting a foot step based on a stride frequency is provided. The method includes the following steps: collecting an original signal in a specified time interval, and performing combined acceleration processing on the original signal to obtain a combined acceleration signal; performing state processing on the combined acceleration signal to obtain a motion time interval, and extracting a plurality of feature groups from the combined acceleration signal according to a preset motion rule; and performing screening on the plurality of feature groups to obtain a first feature group, extracting a median value from the first feature group, obtaining a stride frequency in the specified time interval based on the median value and a collection frequency, and obtaining a quantity of steps through calculation based on the motion time interval and the stride frequency.

In the foregoing technical solution, the plurality of feature groups can be obtained by processing combined foot acceleration information, the median value is extracted from the first feature group in the plurality of feature groups to obtain the stride frequency, and the quantity of steps is obtained by calculating the stride frequency, so that step counting is implemented based on the stride frequency.

In an optional solution of the first aspect, quantity of steps=specified time interval length×motion time ratio/stride frequency; or quantity of steps=motion time interval length/stride frequency.

In another optional solution of the first aspect, the performing state processing on the combined acceleration signal to obtain a motion time interval includes:

dividing the combined acceleration signal into sub-windows at a specified interval, extracting a maximum value, a minimum value, an average value, and a quantity of extreme points from signals in each sub-window, and determining a corresponding state of each sub-window based on the maximum value, the minimum value, the average value, and the quantity of extreme points, where a sum of time intervals of a sub-window corresponding to a walking state and a sub-window corresponding to a running state is the motion time interval.

In still another optional solution of the first aspect, the extracting a plurality of feature groups from the combined acceleration signal according to a preset motion rule includes:

performing differential processing on the combined acceleration signal for a plurality of times to obtain a signal obtained after the differential processing performed for a plurality of times, setting n adjacent values in the signal obtained after the differential processing performed for a plurality of times to one small window, calculating a sum of n values of each small window, and transforming the sum of the n values of each small window into a signal obtained after differential processing performed twice and summation;

searching for a maximum amplitude $M_{max}$ of the signal obtained after the differential processing performed for a plurality of times and summation, and configuring a plurality of threshold lines for the signal obtained after the differential processing performed for a plurality of times and summation, where a difference between two adjacent threshold lines is $M_{max} \times C$ %, and C is a fixed value; and obtaining a quantity m of intersection points of each threshold line and a rising edge of the signal obtained after the differential processing performed for a plurality of times and summation and a value of each intersection point on an X axis, and using m and the value of each intersection point on the X axis as a feature group corresponding to the threshold line, where feature groups corresponding to all threshold lines are the plurality of feature groups.

In a next optional solution of the first aspect, the performing screening on the plurality of feature groups to obtain a first feature group, extracting a median value from the first feature group, and obtaining a stride frequency in the specified time interval based on the median value and a collection frequency includes:

extracting p feature groups from the plurality of feature groups when m falls in a specified range, and calculating a normalized standard difference between values in each of the p feature groups on the X axis;

calculating a difference between a quantity of intersection points of two adjacent feature groups in the p feature groups to obtain a first difference group, calculating a difference between normalized standard differences of values in two adjacent feature groups in the p feature groups on the X axis to obtain a second difference group, extracting an $i^{th}$ value in the first difference group and an $i^{th}$ value in the second difference group for a weighting operation to obtain a plurality of weighting operation results, searching for a $j^{th}$ weighting operation result from front to back that is the first weighting operation result greater than a weighting threshold, and determining a forward feature group of the $j^{th}$ weighting operation result as the first feature group, where both i and j are integers greater than or equal to 1; and extracting a median value from values in the first feature group on the X axis, where stride frequency=median value/sampling frequency.

According to a second aspect, an apparatus for counting a foot step based on a stride frequency is provided. The apparatus includes:

a collection unit, configured to collect an original signal in a specified time interval; and a processing unit, configured to: perform combined acceleration processing on the original signal to obtain a combined acceleration signal; perform state processing on the combined acceleration signal to obtain a motion time interval, and extract a plurality of feature groups from the combined acceleration signal according to a preset motion rule; and perform screening on the plurality of feature groups to obtain a first feature group, extract a median value from the first feature group, obtain a stride frequency in the specified time interval based on the median value and a collection frequency, and obtain a quantity of steps through calculation based on the motion time interval and the stride frequency.

According to a third aspect, a portable device is provided. The device includes a sensor, a processor, a memory, and a transceiver, and the processor is connected to the sensor, the memory, and the transceiver. The sensor is configured to collect an original signal in a specified time interval. The processor is configured to: perform combined acceleration processing on the original signal to obtain a combined acceleration signal; perform state processing on the combined acceleration signal to obtain a motion time interval, and extract a plurality of feature groups from the combined acceleration signal according to a preset motion rule; and perform screening on the plurality of feature groups to obtain a first feature group, extract a median value from the first feature group, obtain a stride frequency in the specified time interval based on the median value and a collection frequency, and obtain a quantity of steps through calculation based on the motion time interval and the stride frequency.

According to a fourth aspect, a computer-readable storage medium is provided. The computer-readable storage medium stores a computer program used to exchange electronic data, and the computer program enables a computer to perform the method provided in the first aspect.

According to a fifth aspect, a computer program product is provided. The computer program product includes a non-transitory computer-readable storage medium storing a computer program, and the computer program can be operated to enable a computer to perform the method provided in the first aspect.

BRIEF DESCRIPTION OF DRAWINGS

To describe the technical solutions in the embodiments of this application or in the prior art more clearly, the following briefly describes the accompanying drawings required for describing the embodiments. Apparently, the accompanying drawings in the following description show merely some embodiments of this application, and a person of ordinary skill in the art may still derive other drawings from these accompanying drawings without creative efforts.

DESCRIPTION OF EMBODIMENTS

The following clearly and completely describes the technical solutions in the embodiments of this application with reference to the accompanying drawings in the embodiments of this application. Apparently, the described embodiments are merely some but not all of the embodiments of this application. All other embodiments obtained by a person of ordinary skill in the art based on the embodiments of this application without creative efforts shall fall within the protection scope of this application.

Figure 1A:
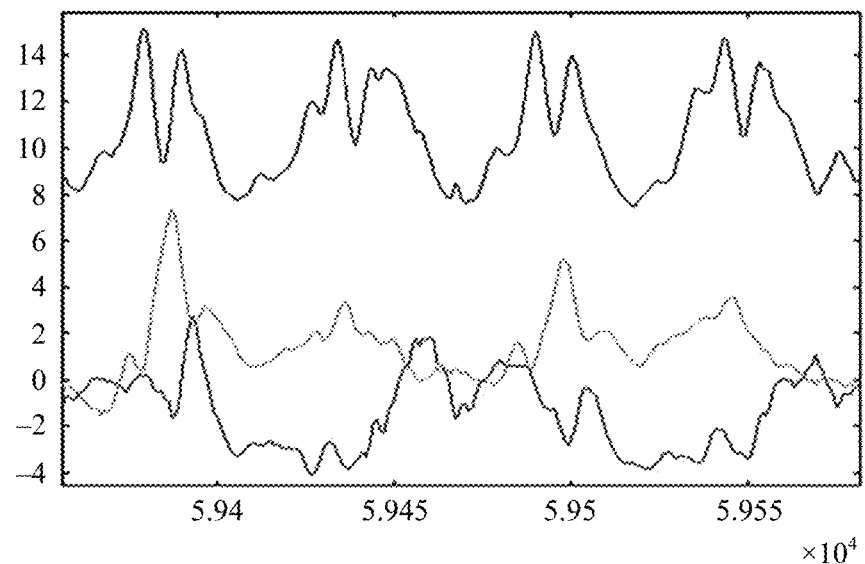
FIG. 1a is a waveform diagram of a hand walking signal.
Figure 1B:
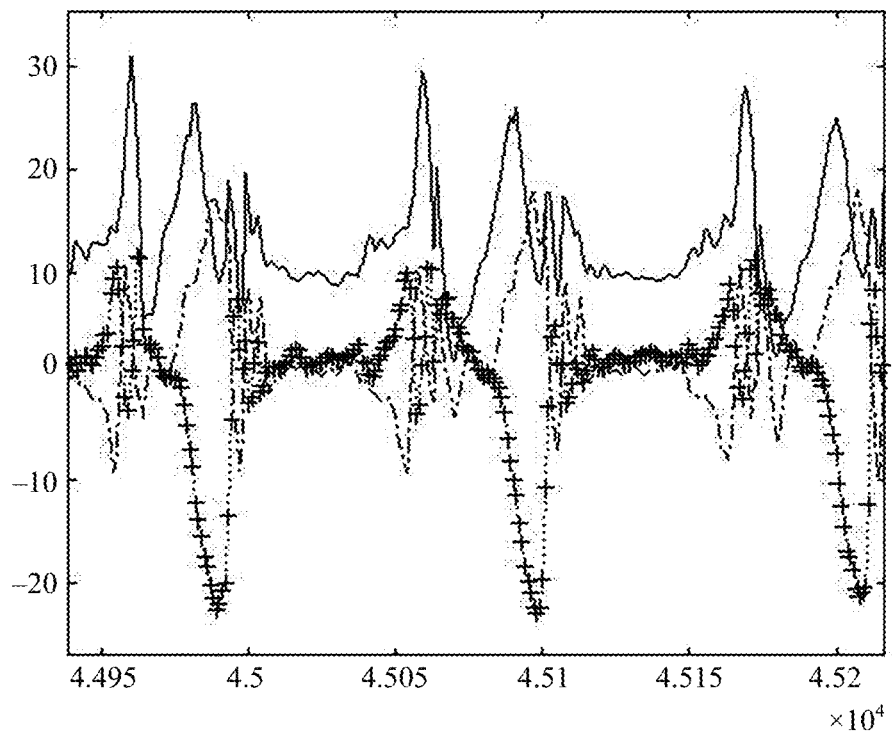
FIG. 1b is a waveform diagram of an ankle walking signal.

FIG. 1a is a waveform diagram of a hand walking signal in a specified time range. FIG. 1b is a waveform diagram of an ankle walking signal in a specified time range. Referring to FIG. 1a, the hand walking signal includes four periods, acceleration amplitude of three axes is relatively small. A major wave peak (including some oscillation) can be seen in each period on an axis perpendicular to the ground, and amplitude keeps changing. Referring to FIG. 1b, the walking signal includes two periods, acceleration amplitude of three axes is relatively large, an axis perpendicular to a ground has two wave peaks in each period, and amplitude does not obviously change in a period. Due to these differences, a hand step counting method is inapplicable to foot step counting.

Figure 2:
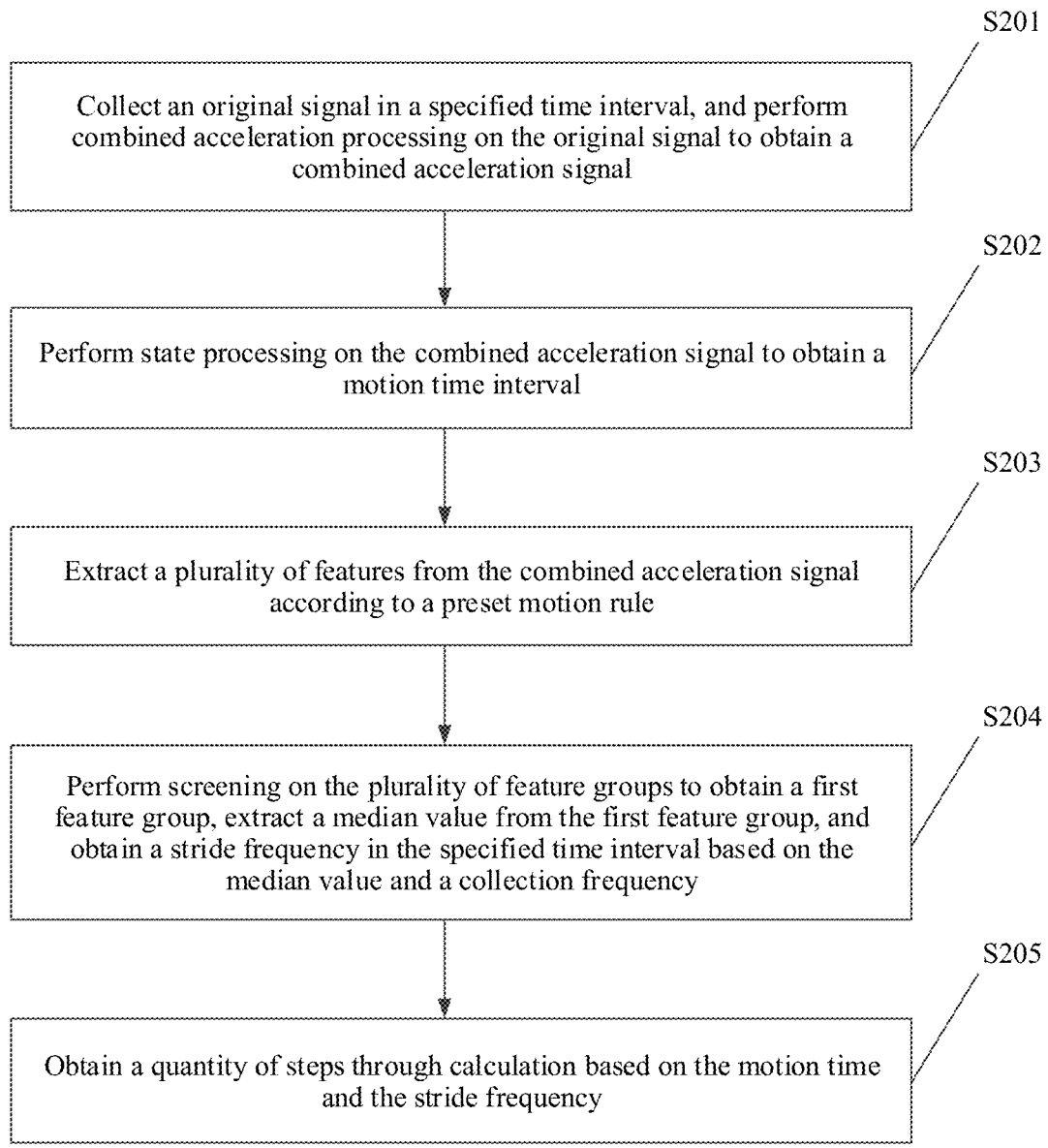
FIG. 2 is a schematic flowchart of a method for counting a foot step based on a stride frequency according to an embodiment of this application.

FIG. 2 provides a method for counting a foot step based on a stride frequency. The method is performed by a wearable device. As shown in FIG. 2, the method includes the following steps.

Step S201. Collect an original signal in a specified time interval, and perform combined acceleration processing on the original signal to obtain a combined acceleration signal.

Figure 2A:
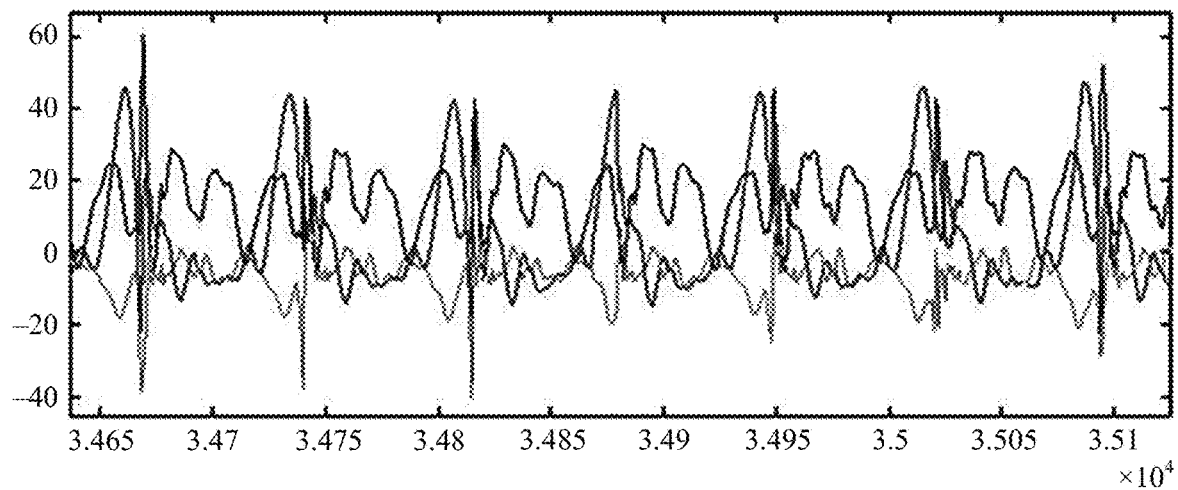
FIG. 2a is an original signal of an ankle collected in a specified time interval according to an embodiment of this application.
Figure 2B:
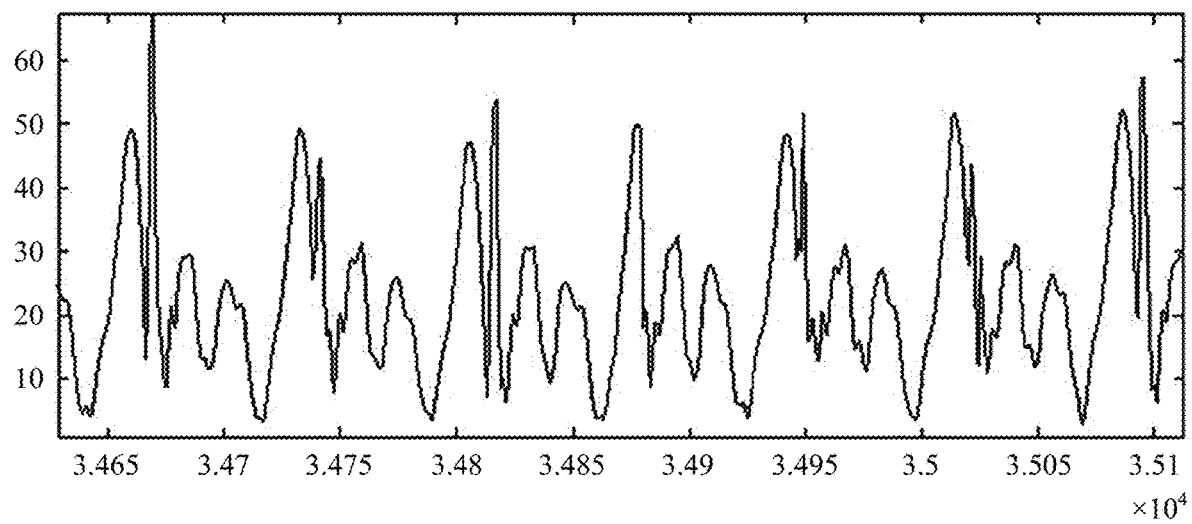
FIG. 2b is a schematic diagram of a combined acceleration signal according to an embodiment of this application.

As shown in FIG. 2a, the original signal in the specified time interval is collected. For example, the specified time interval is 5 s, and as shown in FIG. 2b, the combined acceleration processing is performed on the original signal to obtain the combined acceleration signal. The original signal shown in FIG. 2a may be a three-axis acceleration signal.

Step S202. Process a state of the combined acceleration signal to obtain a motion time interval.

Figure 2C:
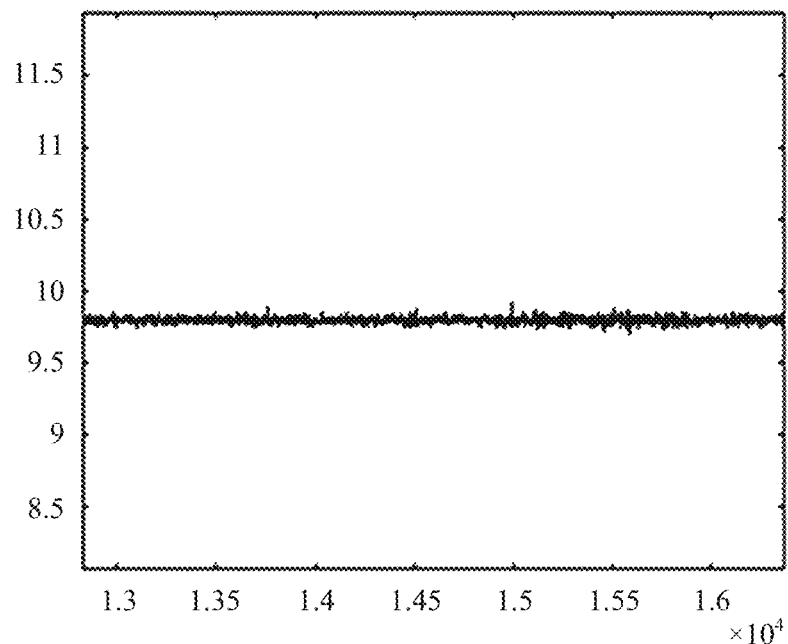
FIG. 2c is a schematic diagram of a typical signal of stillness.
Figure 2D:
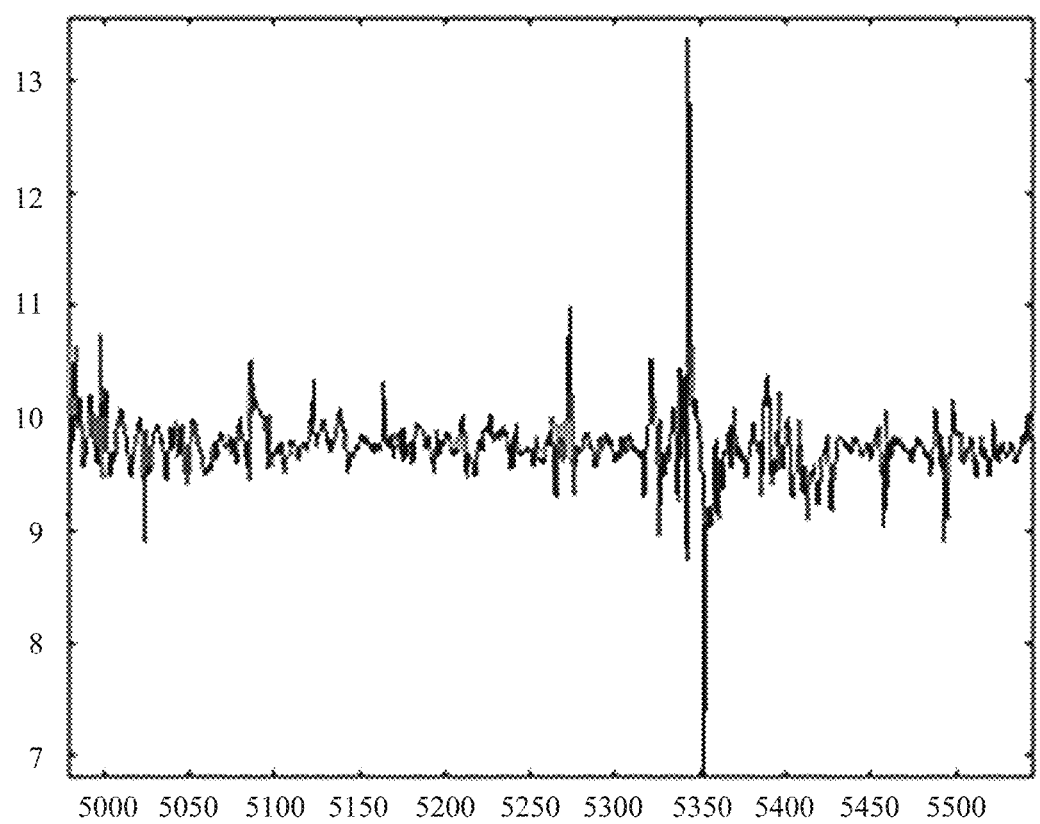
FIG. 2d is a schematic diagram of a typical signal of oscillation.

A state of a signal in the specified time interval is determined. Specifically, combined acceleration is calculated, and the state is determined based on a property of the combined acceleration. The state may specifically include stillness, oscillation, walking, running, and the like. A typical signal of stillness is shown in FIG. 2c. A typical signal of oscillation is shown in FIG. 2d. A signal in a specified amplitude (namely, a Y-axis value) range other than the stillness and the oscillation is determined to a walking or running state. A signal beyond the specified amplitude range is determined to another state. The motion time interval, namely, a sum of a time of walking and a time of running, is obtained after the stillness, the oscillation, and the like are removed.

Specifically, the combined acceleration signal shown in FIG. 2b may be divided into sub-windows at a specified interval (for example, 1 s). A maximum value, a minimum value, an average value, and a quantity of extreme points from signals in each sub-window are extracted. Based on the maximum value, the minimum value, the average value, and a range of the quantity of extreme points, a state corresponding to the range is determined, namely, stillness, oscillation, walking, running, and the like. A sum of time intervals of a sub-window corresponding to a walking state and a sub-window corresponding to a running state is the motion time interval. The average value may be specifically an average value of all signals in the sub-window.

Step S203. Extract a plurality of feature groups from the combined acceleration signal according to a preset motion rule.

Feature extraction aims to find a key feature of each step in an original signal waveform, quantize the key feature, and use the key feature as a main input for counting a quantity of steps, to complete a process from visually observing a form of a waveform to providing a digitalized description. Specifically, as shown in FIG. 2g, combined acceleration of an ankle walking signal may be manually divided into four areas: An area 4 fluctuates most strongly, the other areas fluctuate relatively gently, and an area 1 does not fluctuate basically.

A method for implementing step S203 may be specifically as follows:

Differential processing is performed on the combined acceleration signal for a plurality of times (for example, twice) to obtain a signal obtained after the differential processing performed twice, and n adjacent values in the signal obtained after the differential processing performed twice may be one small window. A sum of n values of each small window is calculated, and the sun of the n values of each small window is transformed into a signal obtained after differential processing performed twice and summation.

Optionally, the value of n is an integer, and u may be a value in [3, 10]. A specific value may be determined based on a frequency of collecting the original signal in the specified time interval. A rule for determining the value of n may be as follows: For example, a higher sampling frequency of the original signal indicates a higher value of n, and a lower sampling frequency of the original signal indicates a lower value of n.

Figure 2E:
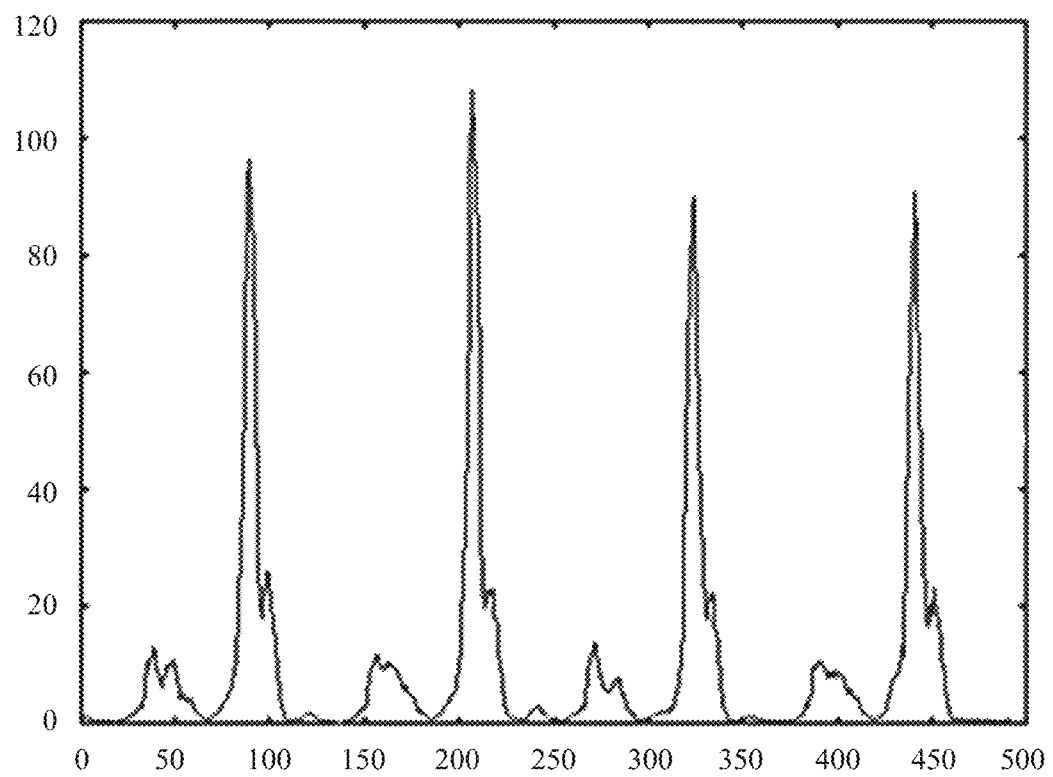
FIG. 2e is a schematic diagram of a signal obtained after differential processing performed twice and summation when n is equal to 6.

FIG. 2e is a schematic diagram of a signal obtained after differential processing performed twice and summation when n is equal to 6.

An example in which the foregoing differential processing is differential processing performed twice is used. Certainly, in actual application, the foregoing differential processing may alternatively be differential processing performed for a plurality of times, for example, differential processing performed for three times and differential processing performed for four times. A specific implementation of this application does not limit a specific quantity of times that differential processing is performed.

Figure 2F:
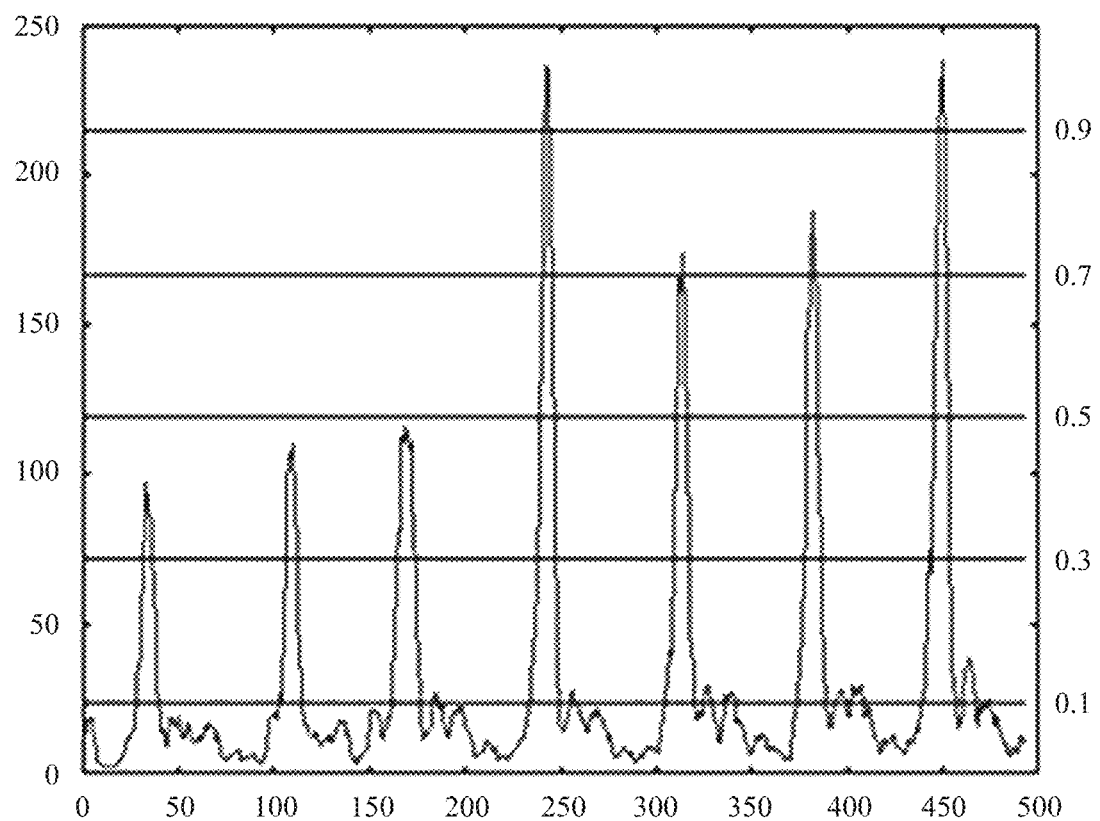
FIG. 2f is a schematic diagram of differential processing performed twice and summation signal for configuring a plurality of threshold lines.
Figure 2G:
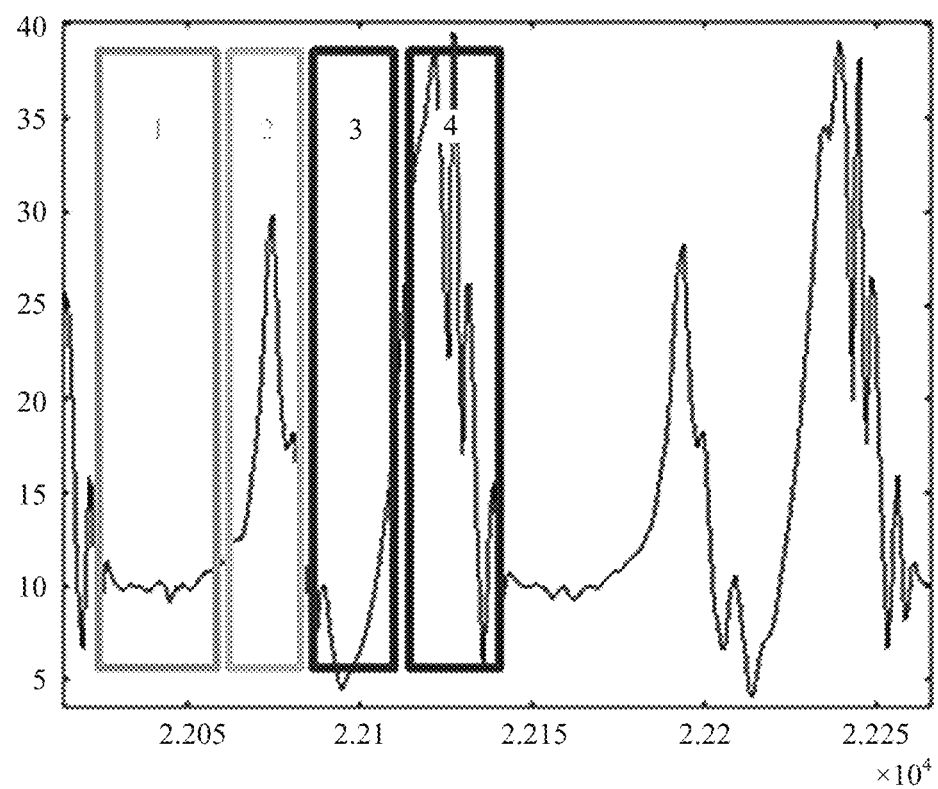
FIG. 2g is a schematic diagram of division of four areas.

A maximum amplitude $M_{max}$ of the signal obtained after the differential processing performed twice and summation is searched for. A plurality of threshold lines are configured for the signal obtained after the differential processing performed twice and summation. A difference between two adjacent threshold lines is $M_{max} \times C$ %, and C is a fixed value (set value). As shown in FIG. 2f, a value of C is 20, to be specific, the difference between the two adjacent threshold lines is $20\% \times X_{max}$. Certainly, in actual application, the value of C may alternatively be 10, 5, or the like.

A quantity m of intersection points of each threshold line and a rising edge of the signal obtained after the differential processing performed twice and summation and a value of each intersection point on an X axis (location) are obtained. The quantity m of intersection points and the value of each intersection point on the X axis are used as a feature group corresponding to the threshold line. Feature groups corresponding to all threshold lines are the plurality of feature groups. Table 1 is a list of values of some feature groups in the plurality of feature groups.

TABLE 1

| Sequence number | Ratio | Quantity (m) | Location (valueon an X axis) |
| --- | --- | --- | --- |
| 1 | 0.7 | 4 | 240, 312, 380, and 446 |
| 2 | 0.6 | 4 | 239, 331, 378, and 445 |
| 3 | 0.5 | 4 | 239, 310, 378, and 445 |
| 4 | 0.4 | 6 | 106, 166, 238, 309, 378, and 000 |

Step S204. Perform screening on the plurality of feature groups to obtain a first feature group, extract a median value from the first feature group, and obtain a stride frequency in the specified time interval based on the median value and a collection frequency.

A method for implementing step S204 may be specifically as follows:

Herein, p feature groups are extracted from the plurality of feature groups, and the quantity of intersection points falls in a specified range. A normalized standard difference between values in each of the p feature groups on the X axis is calculated. Normalized standard difference=standard difference between adjacent differences on the X axis/average value of adjacent differences on the X axis. The average value of adjacent differences on the X axis may be an average value of two adjacent differences on the X axis. Four values are used as an example herein. For ease of description, x1, x2, x3, and x4 are used herein.

Average value of adjacent differences on the X axis=[(x2−x1)+(x3−x2)+(x4−x3)]/3.

Standard difference between adjacent differences on the X axis=standard difference of an array [x2−x1, x3−x2, x4−x3].

A difference between a quantity of intersection points of two adjacent feature groups in the p feature groups to obtain a first difference group. A difference between normalized standard differences of values in two adjacent feature groups in the p feature groups on the X axis to obtain a second difference group. An $i^{th}$ value in the first difference group and an $i^{th}$ value in the second difference group are extracted for a weighting operation to obtain a plurality of weighting operation results. A $j^{th}$ weighting operation result that is the first weighting operation result greater than a weighting threshold is searched for from front to back. A forward feature group of the $j^{th}$ weighting operation result is determined as the first feature group. The weighting operation may be specifically ax+by, where x may be the $i^{th}$ value in the first difference group, y may be the $i^{th}$ value in the second difference group, $i^{th}$ is an integer greater than or equal to 1, and both a and b are preset weight values, and are constants.

Table 2 is used as an example. A difference group (namely, the first difference group) of normalized standard difference is [−0.09, −0.39, 0.04, 0.02, 0.01, 0.50]. A difference group of quantity (namely, the second difference group) is [1, 0, 2, 1, 1, 7]. A weighting operation ax+by is performed on the two difference groups, that is, [a×(−0.09)+b×1, . . . a×0.5+b×7]. Six weighting sums are obtained. Six weighting sums are searched for from front to back. When a weighting sum that is greater than a weighting threshold is found, for example, if a sixth weighting sum meets the condition, the sixth weighting sum is obtained by subtracting the respective feature of a feature group 6 from the respective feature of a feature group 7, so the forward feature group (that is, a decrement) of the sixth weighted sum is the feature group 6. The feature group 6 is a needed feature group. A threshold corresponding to the feature group 6 is an optimum threshold.

A median value of values of an X axis of the first feature group is extracted. Stride frequency=median value/sampling frequency.

The median value is specifically, for example, a plurality of odd numbers. For example, 1, 3, and 7, and the median value is a middle value 3. For example, the plurality of number values are even numbers, and the median value is an average value of two middle values. For example, 1, 3, 5, and 9, median value=(3+5)/2=4.

There are a typical case and a non-typical case in which the first feature group is determined, and may specifically include:

Typical Case

All grounded impact locations are found when an optimal threshold is reached. All the grounded impact locations and leg raising locations are found when a threshold decreases again. It usually occurs when the steps are relatively similar and a leg raising amplitude is less than an impact amplitude.

An adopted determining manner is that, when the threshold decreases, the number of intersection points increases greatly, and a normalized standard difference of a period (a location difference of every two intersection points) increases greatly.

Figure 3A:
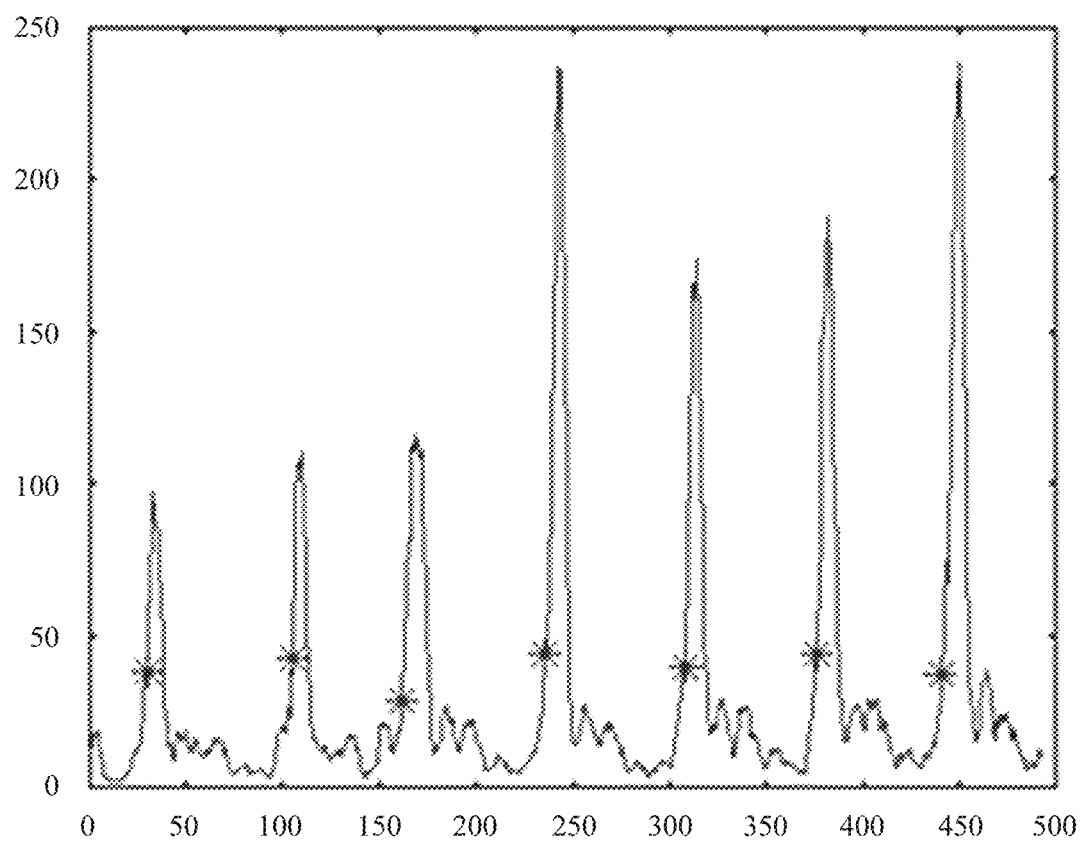
FIG. 3a is a schematic waveform diagram in a typical case.

A method for determining the optimal threshold is to simultaneously consider the foregoing two changes by linear combination, and a threshold that meets the condition is selected. As shown in FIG. 3a, a list of obtained values of p feature groups is shown in Table 2.

TABLE 2

| Sequence number | Normalized standard difference | Quantity (m) |
| --- | --- | --- |
| 1 | 0.51 | 3 |
| 2 | 0.42 | 4 |
| 3 | 0.03 | 4 |
| 4 | 0.07 | 6 |
| 5 | 0.09 | 7 |
| 6 | 0.1 | 7 |
| 7 | 0.61 | 14 |

Based on the data shown in Table 2, it is determined that the number of the first feature group is 6.

Figure 3B:
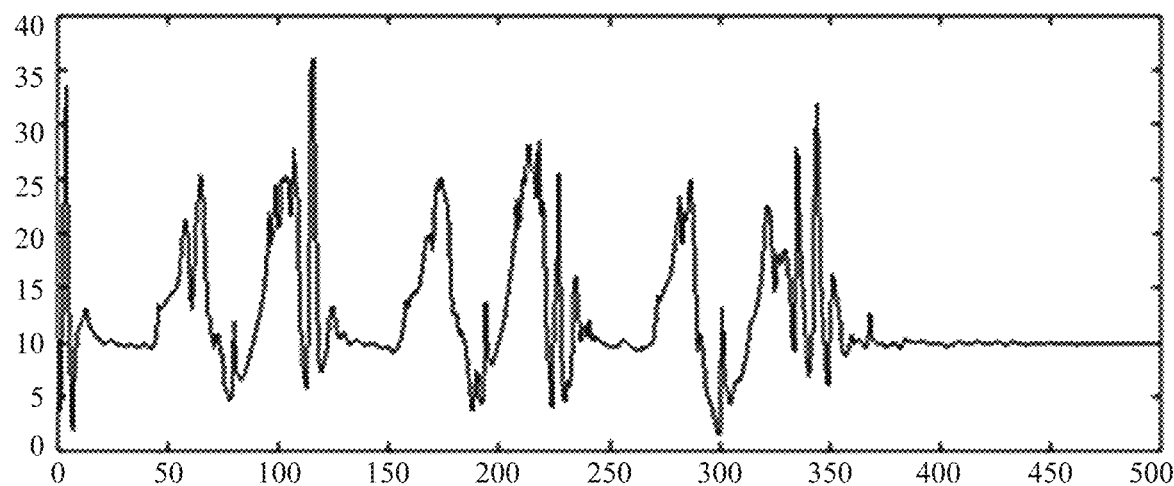
FIG. 3b is a schematic waveform diagram of a combined acceleration signal in non-typical case 1.
Figure 3C:
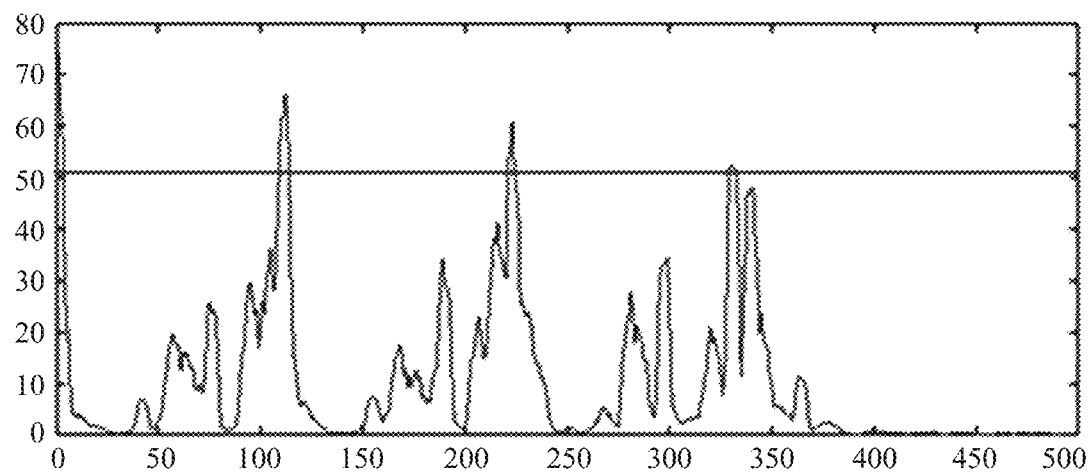
FIG. 3c is a schematic waveform diagram of a signal obtained after differential processing performed twice and summation in non-typical case 1.

Non-typical case 1: As the threshold continuously decreases, impact locations are gradually found, and some leg raising locations are included, which usually occurs when there is a specific difference between each step amplitude, and a leg amplitude and an impact amplitude are not easily distinguished. FIG. 3b is a schematic diagram of a combined acceleration signal in non-typical case 1. FIG. 3c is a schematic diagram of a signal obtained after differential processing performed twice and summation in non-typical case 1. Corresponding data is shown in Table 3. Table 3

TABLE 3

| Sequence number | Normalized standard difference | Quantity (m) | Location (X) |
| --- | --- | --- | --- |
| 1 | 0.02 | 3 | 109, 220, 328 |
| 2 | 0.76 | 4 | 108, 220, 328, and 337 |
| 3 | 0.99 | 5 | 108, 213, 220, 328, and 337 |
| 4 | 0.88 | 7 | . . . |
| 5 | 0.89 | 9 | . . . |
| 6 | 0.98 | 12 | . . . |
| 7 | 0.62 | 9 | . . . |

Based on the data shown in Table 3, it is determined that the number of the first feature group is 1.

Non-Typical Case 2

Figure 3D:
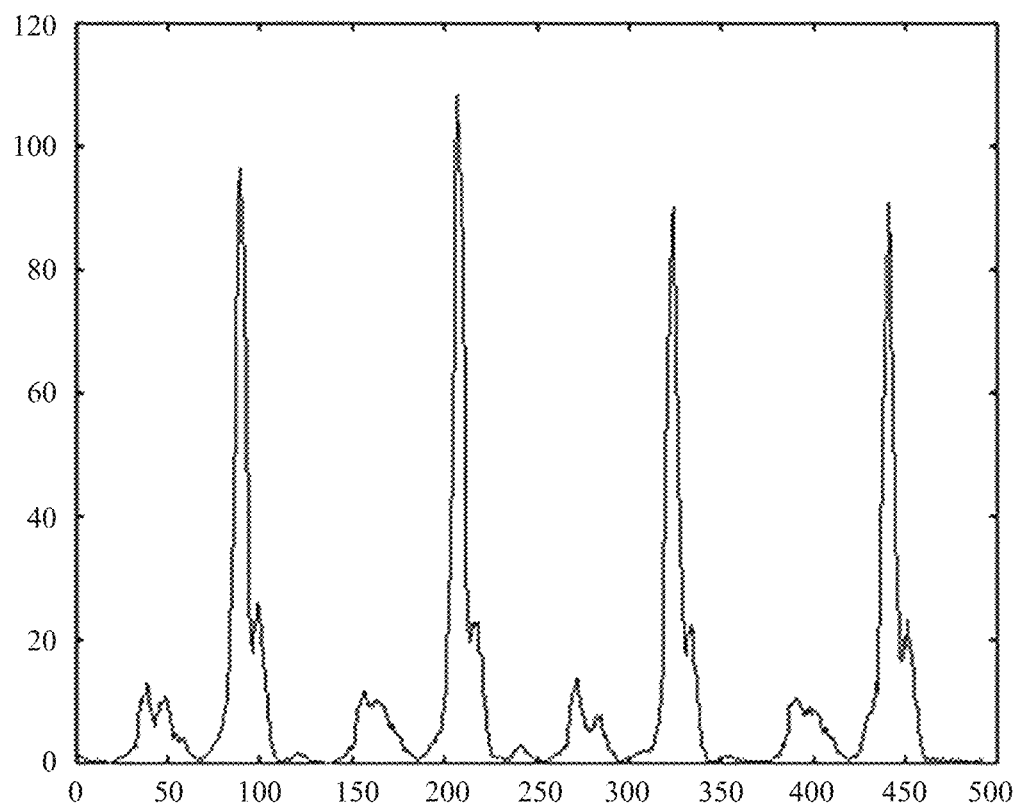
FIG. 3d is a schematic diagram of a signal obtained after differential processing performed twice and summation in non-typical case 2.

As the threshold continuously decreases, all impact locations are found each time, which usually occurs when steps are relatively similar, and when a leg amplitude is far less than an impact amplitude. FIG. 3d is a schematic diagram of a signal obtained after differential processing performed twice and summation in non-typical case 2. Corresponding data is shown in Table 4.

TABLE 4

| Sequence number | Normalized standard difference | Quantity (m) | Location (X) |
| --- | --- | --- | --- |
| 1 | 0.02 | 4 | 83, 201, 318, and 435 |
| 2 | 0.03 | 4 | 82, 200, 317, and 433 |

Based on the data shown in Table 4, it is determined that the number of the first feature group is 2.

Step S205: Calculate based on the motion time and the stride frequency to obtain a quantity of steps.

A method for implementing step S205 may be specifically as follows:

Quantity of steps=specified time interval length×motion time ratio/stride frequency; or quantity of steps=motion time interval length/stride frequency.

Motion time ratio=motion time interval length/specified time interval length.

According to the technical solution provided in this application, step counting processing is performed on a quantity of steps of foot. The technical solution provided in this application has high precision: Step counting is implemented, threshold adaptation is implemented, and accuracy is relatively high. Strong robustness: Processing is performed by searching for data to perform differential processing performed for two times and summation, which is applicable to various periodic data, and only needs signal strength in a period to be different, and there is no special requirement on a signal form. Low complexity: A specific location of each step is not required, and only a stride frequency is required. Calculation is less, which is easy to implement.

Figure 4A:
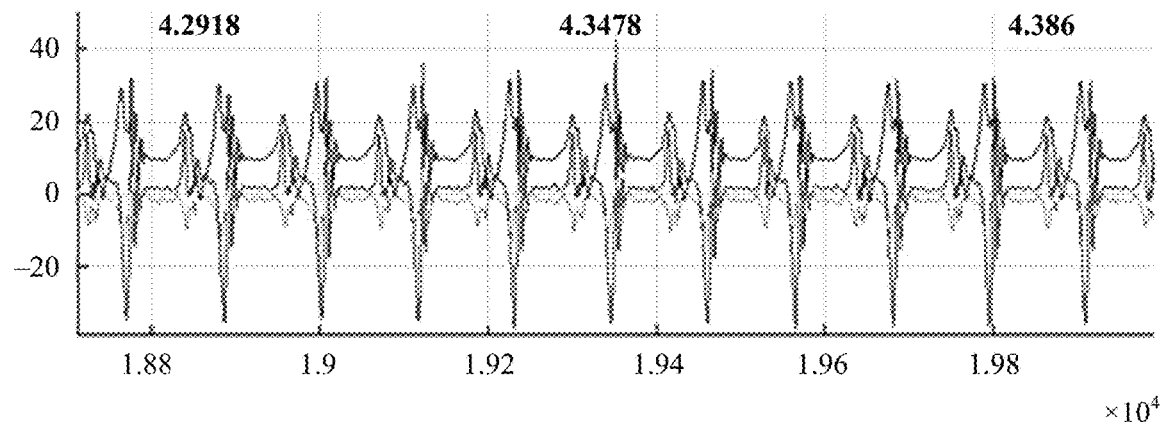
FIG. 4a is a schematic diagram of foot step counting according to this application.

When the technical solution of this application is applied, a step counting result is shown in FIG. 4a based on a three-axis acceleration sensor signal that is collected in advance.

As shown in FIG. 4a, when x axis time is 1.88 to 1.93 (unit: 10^4 ms), a tester walks about 4.4 steps and a step counting result is 4.3478 steps. When the x axis time is 1.93 to 1.98, the tester walks about 4.4 steps, and the step counting result is 4.386 steps.

Figure 4B:
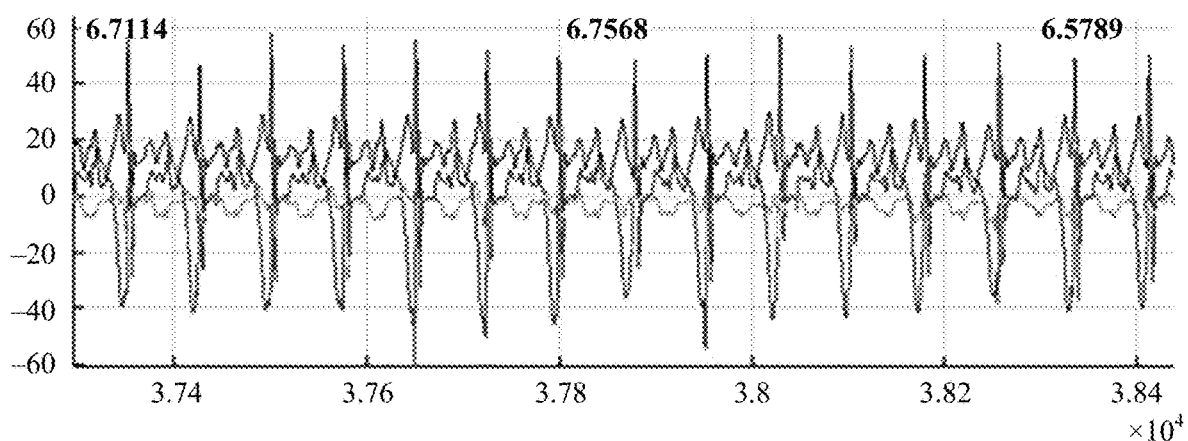
FIG. 4b is another schematic diagram of foot step counting according to this application.

As shown in FIG. 4b, within time 3.73 to 3.78, the tester runs about 6.8 steps, and the step counting result is 6.7568 steps. Within time 3.78 to 3.83, a tester runs about 6.5 steps, and the step counting result is 6.5789 steps.

After preliminary verification, step counting accuracy of a walking/running signal in this application is approximately 97%. An accuracy calculation manner is accuracy=1−abs (quantity of steps calculated by step counting method—real quantity of steps)/real quantity of steps, and abs represents that an absolute value is obtained.

Figure 4C:
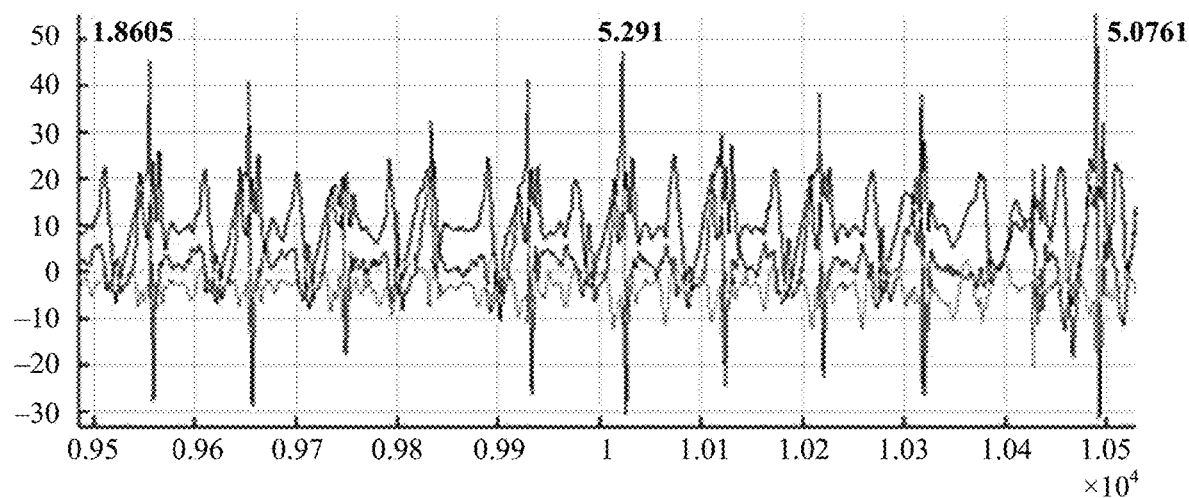
FIG. 4c is still another schematic diagram of foot step counting according to this application.

As shown in FIG. 4c, within time 0.95 to 1, the tester goes downstairs about 5.5 steps, and the step counting result is 5.291 steps. Within time 1 to 1.05, the tester goes downstairs about 5 steps, and the step counting result is 5.0761 steps.

Figure 4D:
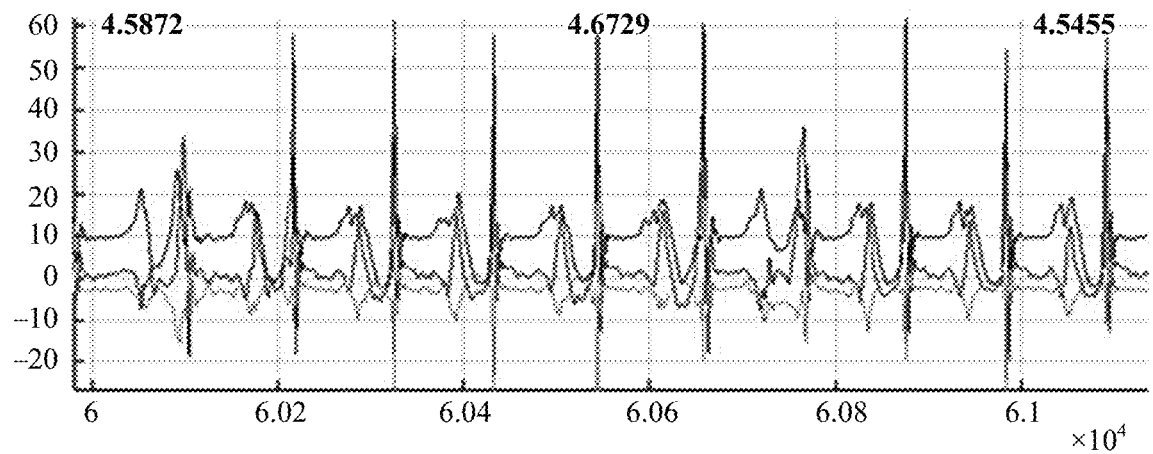
FIG. 4d is yet another schematic diagram of foot step counting according to this application.

As shown in FIG. 4d, within time 6 to 6.05, the tester goes upstairs about 4.7 steps, and the step counting result is 4.6729 steps. Within time 6.05 to 6.1, the tester goes upstairs about 4.5 steps, and the step counting result is 4.5455 steps.

After preliminary verification, step counting accuracy of going upstairs/going downstairs in this application is approximately 95%.

Figure 5A:
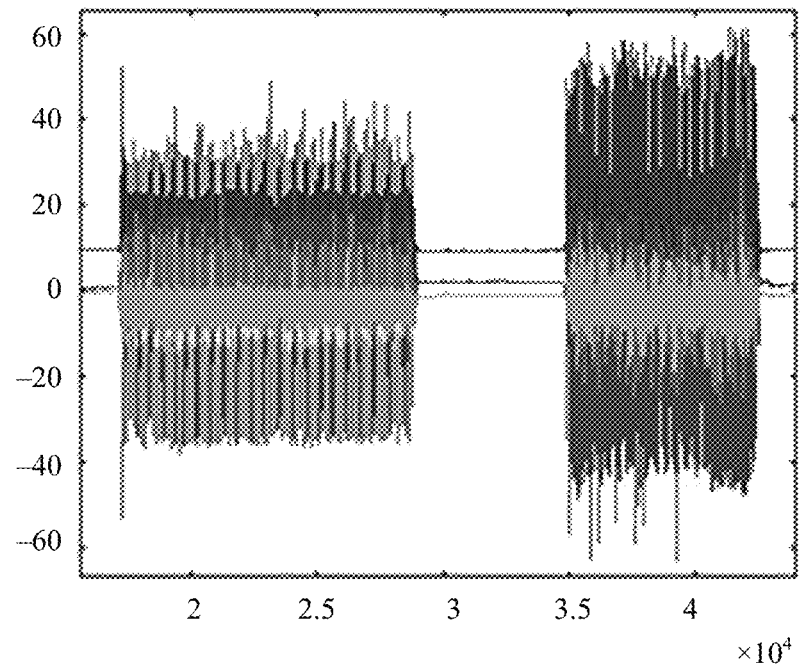
FIG. 5a is a schematic diagram of an original signal according to another embodiment of this application.
Figure 5B:
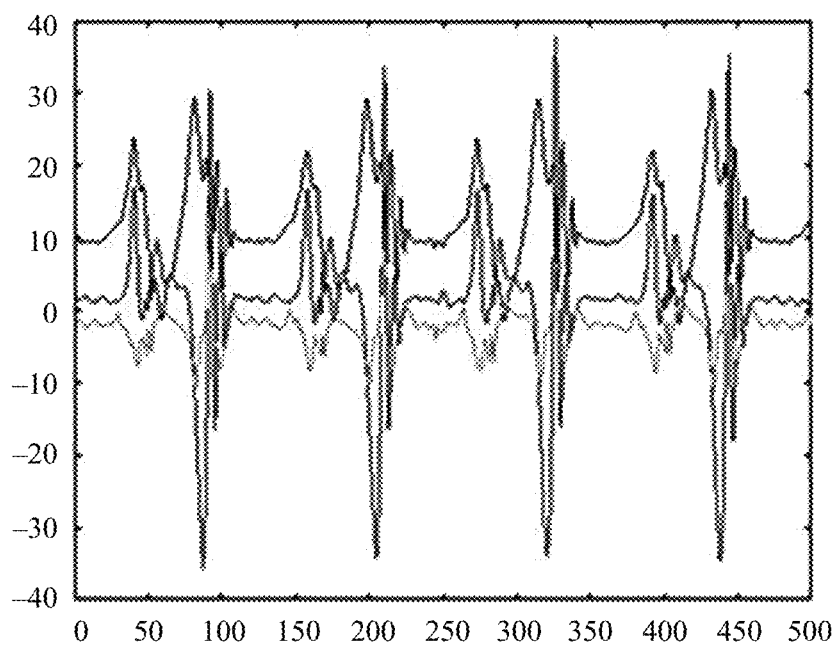
FIG. 5b is a schematic diagram of capturing a 5s window from an original signal according to another embodiment of this application.

This application further provides another embodiment, and how to perform step counting in this application is described by using a foot signal of a tester as an example. As shown in FIG. 5a, the tester walks 200 steps, and runs 210 steps (one step of each foot is recorded as two steps) after a period of time of stillness. As shown in FIG. 5b, a 5s window signal is input.

A state is determined. Specifically, a state of a signal in a window is first determined. Specifically, combined acceleration is calculated, and the state is determined based on a property of the combined acceleration. The state of the signal in this segment is walking.

Then, a time ratio of motion is calculated in segments. Specifically, a signal in a window is segmented by using is as a unit, a state of each segment is determined based on the property of the combined acceleration, and a ratio of walking and running to total time of the window is obtained. A ratio of time of walking (motion) of a signal in this segment is 100%.

Figure 5C:
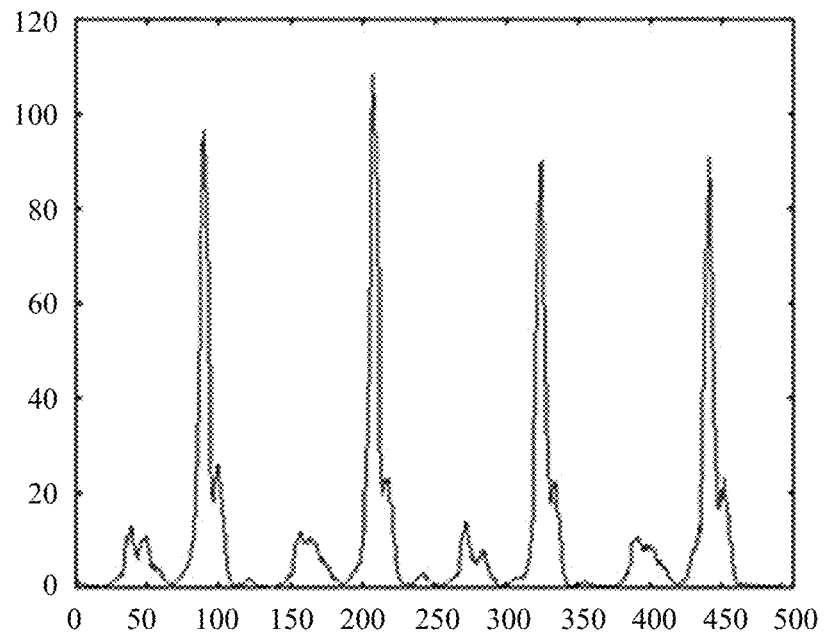
FIG. 5c is a schematic diagram of a signal obtained after differential processing performed twice and summation according to another embodiment of this application.

Feature extraction. Two-time difference is performed on the combined acceleration. Six points are used as one small window and signals obtained after the difference is performed are summed, to obtain a converted two-time difference summation signal (as shown in FIG. 5c).

An initial location of each period is found. The procedure is as follows:

A maximum value of the two-time difference summation signal of the current window is found, and the maximum value of 0.1, 0.2, . . . , 0.9 times is used as a threshold underline. Intersection points between a rising edge of the signal and each threshold are found, and the intersection point is used as the initial location of a group of steps.

According to a basic motion ile, a quantity of intersection points in 5s should be between 3 to 50, and only initial locations that meet the condition and that are of each group are reserved.

A quantity of intersection points of each group, an average value of a period (a location difference of every two intersection points), and a normalized standard difference are calculated.

The initial location of each group is shown in Table 5:

TABLE 5

| Sequence number | Quantity (m) | Location (X) |
|---|---|---|
| 1 | 4 | 83, 201, 318, and 435 |
| 2 | 4 | 82, 200, 317, and 433 |

Stride frequency calculation. After initial locations corresponding to a plurality of groups of thresholds are found, an optimal threshold needs to be determined. Based on the determining manner described above, it may be determined that the window signal belongs to the second non-typical case. For all non-typical cases, a threshold and an initial location corresponding to a minimum normalized standard difference of a period are directly selected, and for this window signal, a first group of initial locations, that is, [83, 201, 318, 435], are selected.

Step quantity calculation. First, reasonableness of a stride frequency is determined. According to the basic motion rule, each step of walking is between 0.5 and 2 s, each step of running is between 0.3 and 1.5 s, the stride frequency is relatively fixed (a normalized standard difference is relatively small), and it can be determined whether a currently calculated stride frequency is reasonable. For this window signal, the normalized standard difference is 0.1443, the stride frequency is 117, which meets a requirement of reasonableness, so it is subjected to the stride frequency calculated this time. Then, a quantity of steps is calculated based on the stride frequency. Quantity of steps=window time length×motion time ratio/stride frequency. The quantity of steps in this window is 4.2735. Finally, the quantity of steps counted in this motion step counting method is 198.9571. Actually, the tester walking and running in total are 205 steps (one step of a wearing foot is counted as one step). The accuracy is 97.05%.

Figure 6:
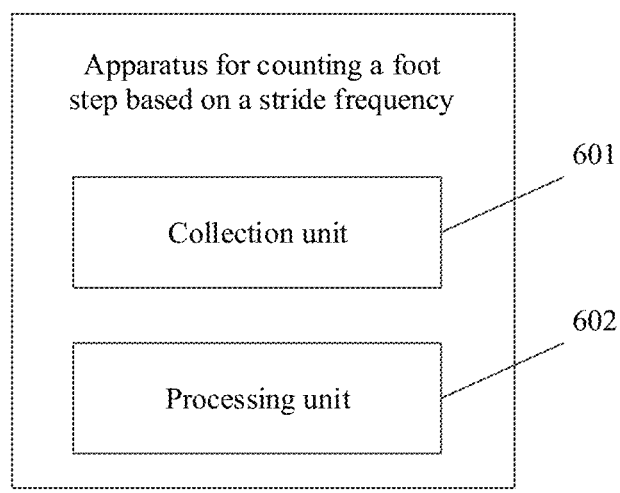
FIG. 6 is a schematic structural diagram of an apparatus for counting a foot step based on a stride frequency according to this application.

FIG. 6 provides an apparatus for counting a foot step based on a stride frequency, and the apparatus includes a collection unit 601 and a processing unit 602.

The collection unit 601 is configured to collect an original signal in a specified time interval.

The processing unit 602 is configured to: perform combined acceleration processing on the original signal to obtain a combined acceleration signal; perform state processing on the combined acceleration signal to obtain a motion time interval, and extract a plurality of feature groups from the combined acceleration signal according to a preset motion rule; and perform screening on the plurality of feature groups to obtain a first feature group, extract a median value from the first feature group, obtain a stride frequency in the specified time interval based on the median value and a collection frequency, and obtain a quantity of steps through calculation based on the motion time interval and the stride frequency.

Optionally, the processing unit 602 is specifically configured to obtain the quantity of steps through calculation based on the motion time interval and the stride frequency to obtain the quantity of steps. Quantity of steps=specified time interval length×motion time ratio/stride frequency.

Alternatively, the processing unit 602 is specifically configured to obtain the quantity of steps through calculation based on the motion time interval and the stride frequency to obtain the quantity of steps. Quantity of steps=motion time interval length/stride frequency.

Optionally, the processing unit 602 is specifically configured to: divide the combined acceleration signal into sub-windows at a specified interval, extract a maximum value, a minimum value, an average value, and a quantity of extreme points from signals in each sub-window, and determine a corresponding state of each sub-window based on the maximum value, the minimum value, the average value, and the quantity of extreme points. A sum of time intervals of a sub-window corresponding to a walking state and a sub-window corresponding to a running state is the motion time interval.

Optionally, the processing unit 602 is specifically configured to: perform differential processing on the combined acceleration signal for a plurality of times to obtain a signal obtained after the differential processing performed for a plurality of times, set n adjacent values in the signal obtained after the differential processing performed for a plurality of times to one small window, calculate a sum of n values of each small window, and transform the sum of the n values of each small window into a signal obtained after differential processing performed twice and summation; search for a maximum amplitude $M_{max}$ of the signal obtained after the differential processing performed for a plurality of times and summation, and configure a plurality of threshold lines for the signal obtained after the differential processing performed for a plurality of times and summation, where a difference between two adjacent threshold lines is $M_{max} \times C$ %, and C is a fixed value; and obtain a quantity m of intersection points of each threshold line and a rising edge of the signal obtained after the differential processing performed for a plurality of times and summation and a value of each intersection point on an X axis, and use m and the value of each intersection point on the X axis as a feature group corresponding to the threshold line, where feature groups corresponding to all threshold lines are the plurality of feature groups.

Optionally, the processing unit 602 is specifically configured to: extract p feature groups from the plurality of feature groups when m falls in a specified range, and calculate a normalized standard difference between values in each of the p feature groups on the X axis; calculate a difference between a quantity of intersection points of two adjacent feature groups in the p feature groups to obtain a first difference group, calculate a difference between normalized standard differences of values in two adjacent feature groups in the p feature groups on the X axis to obtain a second difference group, extract an $i^{th}$ value in the first difference group and an $i^{th}$ value in the second difference group for a weighting operation to obtain a plurality of weighting operation results, search for a $j^{th}$ weighting operation result from front to back that is the first weighting operation result greater than a weighting threshold, and determine a forward feature group of the $j^{th}$ weighting operation result as the first feature group, where both i and j are integers greater than or equal to 1; and extract a median value from values in the first feature group on the X axis, where stride frequency=median value/sampling frequency.

Figure 7:
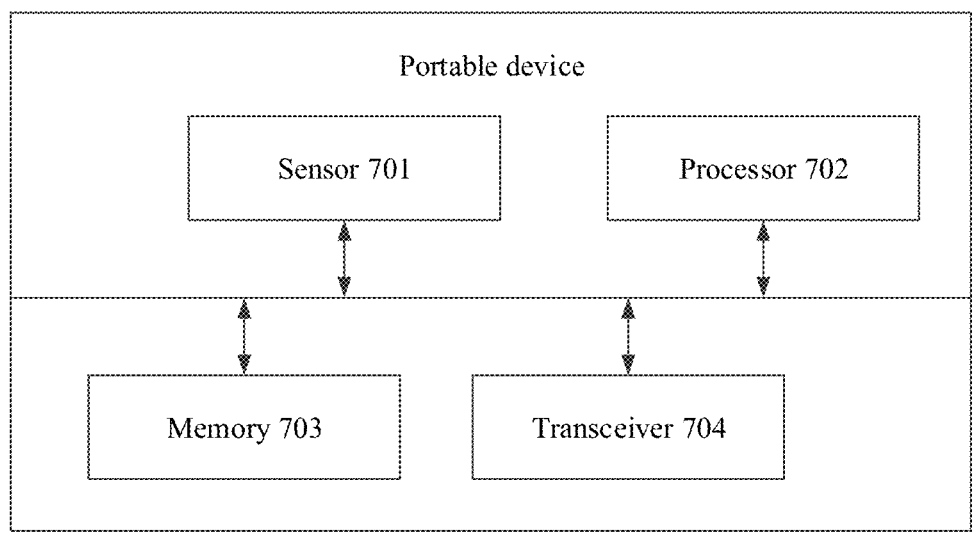
FIG. 7 is a schematic structural diagram of a portable device according to this application.

FIG. 7 further provides a portable device, and the device includes a sensor 701, a processor 702, a memory 703, and a transceiver 704. The processor 702 is connected to the sensor 701, the memory 703, and the transceiver 704.

The sensor 701 is configured to collect an original signal in a specified time interval.

The processor 702 is configured to: perform combined acceleration processing on the original signal to obtain a combined acceleration signal; perform state processing on the combined acceleration signal to obtain a motion time interval, and extract a plurality of feature groups from the combined acceleration signal according to a preset motion rule; and perform screening on the plurality of feature groups to obtain a first feature group, extract a median value from the first feature group, obtain a stride frequency in the specified time interval based on the median value and a collection frequency, and obtain a quantity of steps through calculation based on the motion time interval and the stride frequency.

Optionally, the processor 702 is specifically configured to obtain the quantity of steps through calculation based on the motion time interval and the stride frequency. Quantity of steps=specified time interval length×motion time ratio/stride frequency.

Alternatively, the processor 702 is specifically configured to obtain the quantity of steps through calculation based on the motion time interval and the stride frequency. Quantity of steps=motion time interval length/stride frequency.

Optionally, the processor 702 is specifically configured to: divide the combined acceleration signal into sub-windows at a specified interval, extract a maximum value, a minimum value, an average value, and a quantity of extreme points from signals in each sub-window, and determine a corresponding state of each sub-window based on the maximum value, the minimum value, the average value, and the quantity of extreme points. A sum of time intervals of a sub-window corresponding to a walking state and a sub-window corresponding to a running state is the motion time interval.

Optionally, the processor 702 is specifically configured to: perform differential processing on the combined acceleration signal for a plurality of times to obtain a signal obtained after the differential processing performed for a plurality of times, set n adjacent values in the signal obtained after the differential processing performed for a plurality of times to one small window, calculate a sum of n values of each small window, and transform the sum of the n values of each small window into a signal obtained after differential processing performed twice and summation; search for a maximum amplitude $M_{max}$ of the signal obtained after the differential processing performed for a plurality of times and summation, and configure a plurality of threshold lines for the signal obtained after the differential processing performed for a plurality of times and summation, where a difference between two adjacent threshold lines is $M_{max} \times C$ %, and C is a fixed value; and obtain a quantity m of intersection points of each threshold line and a rising edge of the signal obtained after the differential processing performed for a plurality of times and summation and a value of each intersection point on an X axis, and use m and the value of each intersection point on the X axis as a feature group corresponding to the threshold line, where feature groups corresponding to all threshold lines are the plurality of feature groups.

Optionally, the processor 702 is specifically configured to: extract p feature groups from the plurality of feature groups when m falls in a specified range, and calculate a normalized standard difference between values in each of the p feature groups on the X axis; calculate a difference between a quantity of intersection points of two adjacent feature groups in the p feature groups to obtain a first difference group, calculate a difference between normalized standard differences of values in two adjacent feature groups in the p feature groups on the X axis to obtain a second difference group, extract an $i^{th}$ value in the first difference group and an $i^{th}$ value in the second difference group for a weighting operation to obtain a plurality of weighting operation results, search for a $j^{th}$ weighting operation result from front to back that is the first weighting operation result greater than a weighting threshold, and determine a forward feature group of the $j^{th}$ weighting operation result as the first feature group, where both i and j are integers greater than or equal to 1; and extract a median value from values in the first feature group on the X axis, where stride frequency=median value/sampling frequency.

This application further provides a computer-readable storage medium, and the computer-readable storage medium stores a computer program used to exchange electronic data. The computer program enables a computer to perform the method and the detailed solution shown in FIG. 2.

This application further provides a computer program product. The computer program product includes a non-transitory computer-readable storage medium storing a computer program, and the computer program can be operated to enable a computer to perform the method and the detailed solution shown in FIG. 2.

It should be noted that, for brief description, the foregoing method embodiments are represented as a series of actions. However, a person skilled in the art should appreciate that this application is not limited to the described order of the actions, because according to this application, some steps may be performed in other orders or simultaneously. In addition, it should be further appreciated by a person skilled in the art that the embodiments described in this specification all belong to preferred embodiments, and the involved actions and modules are not necessarily required by this application.

In the foregoing embodiments, the description of each embodiment has respective focuses. For a part that is not described in detail in an embodiment, refer to related descriptions in other embodiments.

In the several embodiments provided in this application, it should be understood that the disclosed apparatus may be implemented in other manners. For example, the described apparatus embodiment is merely an example. For example, the unit division is merely logical function division and may be other division in actual implementation. For example, a plurality of units or components may be combined or integrated into another system, or some features may be ignored or not performed. In addition, the displayed or discussed mutual couplings or direct couplings or communication connections may be implemented through some interfaces. The indirect couplings or communication connections between the apparatuses or units may be implemented in electronic or other forms.

The units described as separate parts may or may not be physically separate, and parts displayed as units may or may not be physical units, may be located in one location, or may be distributed on a plurality of network units. Some or all of the units may be selected based on actual requirements to achieve the objectives of the solutions of the embodiments.

In addition, functional units in the embodiments of this application may be integrated into one processing unit, or each of the units may exist alone physically, or two or more units are integrated into one unit. The integrated unit may be implemented in a form of hardware, or may be implemented in a form of a software functional unit.

When the integrated unit is implemented in the form of a software functional unit and sold or used as an independent product, the integrated unit may be stored in a computer-readable storage. Based on such an understanding, the technical solutions of this application essentially, or the part contributing to the prior art, or all or some of the technical solutions may be implemented in the form of a software product. The software product is stored in a storage medium and includes several instructions for instructing a computer device (which may be a personal computer, a server, or a network device) to perform all or some of the steps of the methods described in the embodiments of this application. The foregoing storage medium includes: any medium that can store program code, such as a USB flash drive, a read-only memory (ROM, Read-Only Memory), a random access memory (RAM, Random Access Memory), a removable hard disk, a magnetic disk, or an optical disc.

What is disclosed above is merely preferred embodiments of this application, and certainly is not intended to limit the protection scope of this application. A person of ordinary skill in the art may understand that all or some of processes that implement the foregoing embodiments and equivalent modifications made in accordance with the claims of this application shall fall within the scope of this application.

What is claimed is:

1. A method executed on a processor of a portable device for counting a foot step based on a stride frequency, the method comprising the steps of:

collecting an original signal in a specified time interval from a sensor in the portable device, and performing combined acceleration processing on the original signal to obtain a combined acceleration signal;

performing state processing on the combined acceleration signal to obtain a motion time interval, and extracting a plurality of feature groups from the combined acceleration signal according to a preset motion rule; and performing screening on the plurality of feature groups to obtain a first feature group, extracting a median value from the first feature group, obtaining a stride frequency in the specified time interval based on the median value and a collection frequency, and obtaining a quantity of steps through calculation based on the motion time interval and the stride frequency;

wherein the performing of state processing on the combined acceleration signal includes dividing the combined acceleration signal into sub-windows at a specified interval, extracting a maximum value, a minimum value, an average value, and a quantity of extreme points from signals in each of the sub-windows, and determining a corresponding state of each of the sub-windows based on a wave peak average value, the maximum value, the minimum value, the average value, and the quantity of extreme points, wherein a sum of time intervals of a sub-window corresponding to a walking state and a sub-window corresponding to a running state is the motion time interval.

2. The method according to claim 1, wherein the quantity of steps is at least one of a length of the specified time interval times a motion time ratio divided by the stride frequency, and the length of the motion time interval divided by the stride frequency.

3. The method according to claim 1, wherein the extracting of the plurality of feature groups comprises:

performing differential processing on the combined acceleration signal for a plurality of times to obtain a signal obtained after the differential processing, setting n adjacent values in the signal obtained after the differential processing to one small window, calculating a sum of n values of each of a plurality of small windows, and transforming the sum of the n values of each of the plurality of small windows into a signal obtained after differential processing and summation, wherein n is an integer greater than 1;

searching for a maximum amplitude Mmax of the signal obtained after the differential processing and summation, and configuring a plurality of threshold lines for the signal obtained after the differential processing and summation, wherein a difference between two adjacent threshold lines is Mmax x C%, and C is a fixed value; and obtaining a quantity m of intersection points of each of the plurality of threshold lines and a rising edge of the signal obtained after the differential processing and summation and a value of each of the intersection points on an X axis, and using m and the value of each of the intersection points on the X axis as a feature group corresponding to the threshold line, wherein feature groups corresponding to all of the plurality of threshold lines are the plurality of feature groups and m is an integer greater than 1.

4. The method according to claim 2, wherein the extracting of the plurality of feature groups comprises:

performing differential processing on the combined acceleration signal for a plurality of times to obtain a signal obtained after the differential processing, setting n adjacent values in the signal obtained after the differential processing to one small window, calculating a sum of n values of each of a plurality of small windows, and transforming the sum of the n values of each of the plurality of small windows into a signal obtained after differential processing and summation, wherein n is an integer greater than 1;

searching for a maximum amplitude Mmax of the signal obtained after the differential processing and summation, and configuring a plurality of threshold lines for the signal obtained after the differential processing and summation, wherein a difference between two adjacent threshold lines is Mmax x C%, and C is a fixed value; and obtaining a quantity m of intersection points of each of the plurality of threshold lines and a rising edge of the signal obtained after the differential processing and summation and a value of each of the intersection points on an X axis, and using m and the value of each of the intersection points on the X axis as a feature group corresponding to the threshold line, wherein feature groups corresponding to all of the plurality of threshold lines are the plurality of feature groups and m is an integer greater than 1.

5. The method according to claim 3, wherein the performing of screening on the plurality of feature groups comprises:

extracting p feature groups from the plurality of feature groups when m falls in a specified range, and calculating a normalized standard difference between values in each of the p feature groups on the X axis, wherein p is an integer greater than 2; and calculating a difference between a quantity of intersection points of two adjacent feature groups in the p feature groups to obtain a first difference group, calculating a difference between normalized standard differences of values in two adjacent feature groups in the p feature groups on the X axis to obtain a second difference group, extracting an ith value in the first difference group and an ith value in the second difference group for a weighting operation to obtain a plurality of weighting operation results, searching for a jth weighting operation result from front to back that is a first weighting operation result greater than a weighting threshold, and determining a forward feature group of the jth weighting operation result as the first feature group, wherein both i and j are integers greater than or equal to 1, wherein the extracting of the median value extracts the median value from values in the first feature group on the X axis, and wherein the obtaining of the stride frequency obtains the stride frequency by dividing the median value by a sampling frequency.

6. The method according to claim 4, wherein the performing of screening on the plurality of feature groups comprises:

extracting p feature groups from the plurality of feature groups when m falls in a specified range, and calculating a normalized standard difference between values in each of the p feature groups on the X axis, wherein p is an integer greater than 2; and calculating a difference between a quantity of intersection points of two adjacent feature groups in the p feature groups to obtain a first difference group, calculating a difference between normalized standard differences of values in two adjacent feature groups in the p feature groups on the X axis to obtain a second difference group, extracting an ith value in the first difference group and an ith value in the second difference group for a weighting operation to obtain a plurality of weighting operation results, searching for a jth weighting operation result from front to back that is a first weighting operation result greater than a weighting threshold, and determining a forward feature group of the jth weighting operation result as the first feature group, wherein both i and j are integers greater than or equal to 1, wherein the extracting of the median value extracts the median value from values in the first feature group on the X axis, and wherein the obtaining of the stride frequency obtains the stride frequency by dividing the median value by a sampling frequency.

7. A portable device, comprising: a sensor; a processor; a memory; and a transceiver,
   wherein the processor is connected to the sensor, the memory, and the transceiver,
   wherein the sensor is configured to collect an original signal in a specified time interval,
   wherein the processor is configured to:
       perform combined acceleration processing on the original signal to obtain a combined acceleration signal;
       perform state processing on the combined acceleration signal to obtain a motion time interval, and extract a plurality of feature groups from the combined acceleration signal according to a preset motion rule; and
       perform screening on the plurality of feature groups to obtain a first feature group, extract a median value from the first feature group, obtain a stride frequency in the specified time interval based on the median value and a collection frequency, and obtain a quantity of steps through calculation based on the motion time interval and the stride frequency;
   wherein for the performing of the state processing on the combined acceleration signal, the processor is further configured to divide the combined acceleration signal into sub-windows at a specified interval, extract a maximum value, a minimum value, an average value, and a quantity of extreme points from signals in each of the sub-windows, and determine a corresponding state of each of the sub-windows based on the maximum value, the minimum value, the average value, and the quantity of extreme points, and
   wherein a sum of time intervals of a sub-window corresponding to a walking state and a sub-window corresponding to a running state is the motion time interval.

8. The device according to claim 7, wherein the quantity of steps is at least one of a length of the specified time interval times a motion time ratio divided by the stride frequency, and the length of the motion time interval divided by the stride frequency.

9. The device according to claim 7, wherein for the extracting of the plurality of feature groups, the processor is further configured to:
   perform differential processing on the combined acceleration signal for a plurality of times to obtain a signal obtained after the differential processing, set n adjacent values in the signal obtained after the differential processing to one small window, calculate a sum of n values of each of a plurality of small windows, and transform the sum of the n values of each of the plurality of small windows into a signal obtained after differential processing and summation, wherein n is an integer greater than 1;
   search for a maximum amplitude Mmax of the signal obtained after the differential processing and summation, and configure a plurality of threshold lines for the signal obtained after the differential processing and summation, wherein a difference between two adjacent threshold lines is Mmax x C%, and C is a fixed value; and
   obtain a quantity m of intersection points of each of the plurality of threshold lines and a rising edge of the signal obtained after the differential processing and summation and a value of each of the intersection points on an X axis, and using m and the value of each of the intersection points on the X axis as a feature group corresponding to the threshold line, wherein feature groups corresponding to all of the plurality of threshold lines are the plurality of feature groups and m is an integer greater than 1.

10. The device according to claim 8, wherein for the extracting of the plurality of feature groups, the processor is further configured to:
    perform differential processing on the combined acceleration signal for a plurality of times to obtain a signal obtained after the differential processing, set n adjacent values in the signal obtained after the differential processing to one small window, calculate a sum of n values of each of a plurality of small windows, and transform the sum of the n values of each of the plurality of small windows into a signal obtained after differential processing and summation, wherein n is an integer greater than 1;
    search for a maximum amplitude Mmax of the signal obtained after the differential processing and summation, and configure a plurality of threshold lines for the signal obtained after the differential processing and summation, wherein a difference between two adjacent threshold lines is Mmax x C%, and C is a fixed value; and
    obtain a quantity m of intersection points of each of the plurality of threshold lines and a rising edge of the signal obtained after the differential processing and summation and a value of each of the intersection points on an X axis, and using m and the value of each of the intersection points on the X axis as a feature group corresponding to the threshold line, wherein feature groups corresponding to all of the plurality of threshold lines are the plurality of feature groups and m is an integer greater than 1.

11. The device according to claim 9,
    wherein for the performing of screening on the plurality of feature groups, the processor is further configured to:
        extract p feature groups from the plurality of feature groups when m falls in a specified range, and calculate a normalized standard difference between values in each of the p feature groups on the X axis, wherein p is an integer greater than 2; and
        calculate a difference between a quantity of intersection points of two adjacent feature groups in the p feature groups to obtain a first difference group, calculate a difference between normalized standard differences of values in two adjacent feature groups in the p feature groups on the X axis to obtain a second difference group, extract an ith value in the first difference group and an ith value in the second difference group for a weighting operation to obtain a plurality of weighting operation results, search for a jth weighting operation result from front to back that is a first weighting operation result greater than a weighting threshold, and determine a forward feature group of the jth weighting operation result as the first feature group, wherein both i and j are integers greater than or equal to 1, wherein for the extracting of the median value, the processor is further configured to extract the median value from values in the first feature group on the X axis, and wherein for the obtaining of the stride frequency, the processor is further configured to obtain the stride frequency by dividing the median value by a sampling frequency.

12. The device according to claim 9, wherein for the performing of screening on the plurality of feature groups, the processor is further configured to:

extract p feature groups from the plurality of feature groups when m falls in a specified range, and calculate a normalized standard difference between values in each of the p feature groups on the X axis, wherein p is an integer greater than 2; and calculate a difference between a quantity of intersection points of two adjacent feature groups in the p feature groups to obtain a first difference group, calculate a difference between normalized standard differences of values in two adjacent feature groups in the p feature groups on the X axis to obtain a second difference group, extract an ith value in the first difference group and an ith value in the second difference group for a weighting operation to obtain a plurality of weighting operation results, search for a jth weighting operation result from front to back that is a first weighting operation result greater than a weighting threshold, and determine a forward feature group of the jth weighting operation result as the first feature group, wherein both i and j are integers greater than or equal to 1, wherein for the extracting of the median value, the processor is further configured to extract the median value from values in the first feature group on the X axis, and wherein for the obtaining of the stride frequency, the processor is further configured to obtain the stride frequency by dividing the median value by a sampling frequency.

13. A non-transitory computer-readable storage medium for storing one or more programs, wherein the one or more programs comprise an instruction, and when the instruction is executed by a processor in a portable device, the processor performs the following operations:

collecting an original signal in a specified time interval from a sensor in the portable device, and performing combined acceleration processing on the original signal to obtain a combined acceleration signal;

performing state processing on the combined acceleration signal to obtain a motion time interval, and extracting a plurality of feature groups from the combined acceleration signal according to a preset motion rule; and performing screening on the plurality of feature groups to obtain a first feature group, extracting a median value from the first feature group, obtaining a stride frequency in the specified time interval based on the median value and a collection frequency, and obtaining a quantity of steps through calculation based on the motion time interval and the stride frequency;

wherein the performing of state processing on the combined acceleration signal includes dividing the combined acceleration signal into sub-windows at a specified interval, extracting a maximum value, a minimum value, an average value, and a quantity of extreme points from signals in each of the sub-windows, and determining a corresponding state of each of the sub-windows based on a wave peak average value, the maximum value, the minimum value, the average value, and the quantity of extreme points, wherein a sum of time intervals of a sub-window corresponding to a walking state and a sub-window corresponding to a running state is the motion time interval.

14. The non-transitory computer-readable storage medium according to claim 13, wherein the quantity of steps is at least one of a length of the specified time interval times a motion time ratio divided by the stride frequency, and the length of the motion time interval divided by the stride frequency.

15. The non-transitory computer-readable storage medium according to claim 13, wherein the extracting the plurality of feature groups comprises:

performing differential processing on the combined acceleration signal for a plurality of times to obtain a signal obtained after the differential processing, setting n adjacent values in the signal obtained after the differential processing to one small window, calculating a sum of n values of each of a plurality of small windows, and transforming the sum of the n values of each of the plurality of small windows into a signal obtained after differential processing and summation, wherein n is an integer greater than 1;

searching for a maximum amplitude Mmax of the signal obtained after the differential processing performed for a plurality of times and summation, and configuring a plurality of threshold lines for the signal obtained after the differential processing and summation, wherein a difference between two adjacent threshold lines is Mmax x C%, and C is a fixed value; and obtaining a quantity m of intersection points of each of the plurality of threshold lines and a rising edge of the signal obtained after the differential processing and summation and a value of each of the intersection points on an X axis, and using m and the value of each of the intersection points on the X axis as a feature group corresponding to the threshold line, wherein feature groups corresponding to all of the plurality of threshold lines are the plurality of feature groups and m is an integer greater than 1.

16. The non-transitory computer-readable storage medium according to claim 14, wherein the extracting of the plurality of feature groups comprises:

performing differential processing on the combined acceleration signal for a plurality of times to obtain a signal obtained after the differential processing, setting n adjacent values in the signal obtained after the differential processing to one small window, calculating a sum of n values of each of a plurality of small windows, and transforming the sum of the n values of each of the plurality of small windows into a signal obtained after differential processing and summation, wherein n is an integer greater than 1;

searching for a maximum amplitude Mmax of the signal obtained after the differential processing and summation, and configuring a plurality of threshold lines for the signal obtained after the differential processing and summation, wherein a difference between two adjacent threshold lines is Mmax x C%, and C is a fixed value; and obtaining a quantity m of intersection points of each of the plurality of threshold lines and a rising edge of the signal obtained after the differential processing and summation and a value of each of the intersection points on an X axis, and using m and the value of each of the intersection points on the X axis as a feature group corresponding to the threshold line, wherein feature groups corresponding to all of the plurality of threshold lines are the plurality of feature groups and m is an integer greater than 1.

17. The non-transitory computer-readable storage medium according to claim 15, wherein the performing of screening on the plurality of feature groups comprises:
   extracting p feature groups from the plurality of feature groups when m falls in a specified range, and calculating a normalized standard difference between values in each of the p feature groups on the X axis, wherein p is an integer greater than 2;
   calculating a difference between a quantity of intersection points of two adjacent feature groups in the p feature groups to obtain a first difference group, calculating a difference between normalized standard differences of values in two adjacent feature groups in the p feature groups on the X axis to obtain a second difference group, extracting an ith value in the first difference group and an ith value in the second difference group for a weighting operation to obtain a plurality of weighting operation results, searching for a jth weighting operation result from front to back that is a first weighting operation result greater than a weighting threshold, and determining a forward feature group of the jth weighting operation result as the first feature group, wherein both i and j are integers greater than or equal to 1,
   wherein the extracting of the median value extracts the median value from values in the first feature group on the X axis, and
   wherein the obtaining of the stride frequency obtains the stride frequency by dividing the median value by a sampling frequency.

18. The non-transitory computer-readable storage medium according to claim 16, wherein the performing of screening on the plurality of feature groups comprises:
   extracting p feature groups from the plurality of feature groups when m falls in a specified range, and calculating a normalized standard difference between values in each of the p feature groups on the X axis, wherein p is an integer greater than 2;
   calculating a difference between a quantity of intersection points of two adjacent feature groups in the p feature groups to obtain a first difference group, calculating a difference between normalized standard differences of values in two adjacent feature groups in the p feature groups on the X axis to obtain a second difference group, extracting an ith value in the first difference group and an ith value in the second difference group for a weighting operation to obtain a plurality of weighting operation results, searching for a jth weighting operation result from front to back that is a first weighting operation result greater than a weighting threshold, and determining a forward feature group of the jth weighting operation result as the first feature group, wherein both i and j are integers greater than or equal to 1,
   wherein the extracting of the median value extracts the median value from values in the first feature group on the X axis, and
   wherein the obtaining of the stride frequency obtains the stride frequency by dividing the median value by a sampling frequency.

* * * * *